(12) United States Patent
Cartiglia et al.

(10) Patent No.: US 9,921,318 B2
(45) Date of Patent: Mar. 20, 2018

(54) DEVICES FOR THE SIMULTANEOUS MEASUREMENT IN REAL TIME OF ENERGY AND OF FLUX OF MONO-ENERGETIC BEAMS OF HADRONS OF LOW ENERGY

(71) Applicant: ISTITUTO NAZIONALE DI FISICA NUCLEARE, Frascati (IT)

(72) Inventors: Nicoló Cartiglia, Milan (IT); Roberto Sacchi, Turin (IT)

(73) Assignee: ISTITUTO NAZIONALE DI FISICA NUCLEARE, Frascati (IT)

( * ) Notice: Subject to any disclaimer, the term of this patent is extended or adjusted under 35 U.S.C. 154(b) by 0 days.

(21) Appl. No.: 15/316,855

(22) PCT Filed: Jun. 10, 2015

(86) PCT No.: PCT/IB2015/054383
§ 371 (c)(1),
(2) Date: Dec. 7, 2016

(87) PCT Pub. No.: WO2015/189782
PCT Pub. Date: Dec. 17, 2015

(65) Prior Publication Data
US 2017/0115407 A1    Apr. 27, 2017

(30) Foreign Application Priority Data

Jun. 10, 2014   (IT) .............................. TO2014A0464

(51) Int. Cl.
*G01T 1/24*    (2006.01)
*G01T 1/29*    (2006.01)
(Continued)

(52) U.S. Cl.
CPC .............. *G01T 1/29* (2013.01); *A61N 5/1048* (2013.01); *G01N 15/1459* (2013.01); *A61N 2005/1087* (2013.01); *G01N 2015/1486* (2013.01)

(58) Field of Classification Search
CPC .......... A61N 2005/1087; A61N 5/1048; A61N 5/1075; A61N 2005/1052; A61N 5/1049;
(Continued)

(56) References Cited

U.S. PATENT DOCUMENTS

| 2012/0104270 A1* | 5/2012 | Marchand | G01T 1/2935 |
| | | | 250/389 |
| 2013/0068956 A1* | 3/2013 | Friedman | G01T 1/26 |
| | | | 250/382 |
| 2015/0217139 A1* | 8/2015 | Bert | A61N 5/1043 |
| | | | 600/1 |

OTHER PUBLICATIONS

N. Cartiglia, M.Baselga, G. Dellacasa, S. Ely, V. Fadeyev, Z. Galloway, S. Garbolino, F. Marchetto, S. Martoiu, G. Mazza, J. Ngo, M. Obertino, C. Parker, A. Rivetti, D. Shumacher, H.F-W. Sadrozinski, A. Seiden, A. Zatserklyaniy, Performance of ultra-fast silicon detectors, IOP Publishing for Sissa Medialab srl, 13th Topical Seminar of Innovative Particle and Radiation Detectors, Oct. 7-10, 2013, Feb. 4, 2014, 2014 Jinst 9 C02001, doi:10.1088/1748-0221/9/02/C02001, pp. 1-10, Siena, Italy.

(Continued)

*Primary Examiner* — Taeho Jo
(74) *Attorney, Agent, or Firm* — Robert E. Alderson, Jr.

(57) ABSTRACT

Systems and methods for measuring mono-energetic hadron beams are provided. Such systems and methods include a first detection unit having a planar sensor with a sensing area segmented into a matrix of pixels, each pixel being adapted to provide a transit signal indicative of transit of a particle therethrough, and a counting circuit coupled to the sensor for providing an output signal indicative of number of particles (Continued)

$N_p$ of the beam crossing said sensing area in a time interval, based on the transit signals provided by said pixels, and a second detection unit arranged downstream of the first detection unit which includes at least one ionization detector for providing an output signal proportional to the total charge $Q_{ion}$ released by the beam (B) in the ionization detector in such time interval.

8 Claims, 2 Drawing Sheets

(51) Int. Cl.
    *G01N 15/14*     (2006.01)
    *A61N 5/10*     (2006.01)

(58) Field of Classification Search
    CPC ....... G01N 15/1031; G01N 2015/0038; G01N 2015/1062
    USPC .................................................... 250/370.14
    See application file for complete search history.

(56) References Cited

OTHER PUBLICATIONS

G. Pellegrini, P. Fernandez-Martinez, M. Baselga, C. Fleta, D. Flores, V. Greco, S. Hidalgo, I. Mandic, G. Kramberger, D. Quirion, M. Ullan, Technology developments and first measurements of Low Gain Avalanche Detectors (LGAD) for high energy physics applications, Nuclear Instruments and Methods in Physics Research A, www.elsevier.com/locate/nima,http://dx.doi.org/10.1016/j.nima.2014.06.008, 2014, Elsevier, Spain.

H.F.-W. Sadrozinski, S. Ely, V. Fadeyev, Z. Galloway, J. Ngo, C. Parker, B. Petersen, A.Seiden, A. Zatserklyaniy, N. Cartiglia, F. Marchetto, M. Bruzzi, R. Mori, M. Scaringella, A. Vinattieri, Ultra fast silicon detectors, Nuclear Instruments and Methods in Physics Research A, www.elsevier.com/locate/nima, 0168-9002, http://dx.doi.org/10.1016/j.nima.2013.06.033, 2013, Elsevier.

S. Giordanengo, M. Donetti, M.A. Garella, F. Marchetto, G. Alampi, A. Ansarinejad, V. Monaco, M.Mucchi, I.A.Pecka, C.Peroni, R.Sacchi, M.Scalise, C.Tomba, R.Cirio, Design and characterization of the beam monitor detectors of the Italian National Center of Oncological Hadron-therapy (CNAO), Nuclear Instruments and Methods in Physics Research A, www.elsevier.com/locate/nima,http://dx.doi.org/10.1016/j.nima.2012.10.004, 0168-9002, 2012, Elsevier.

M.Rebisz-Pomorska, M.Ciobanu, M.Kis, M. Pomorski, B.Voss, Diamond detectors for the monitoring of carbon-ion therapy beams, Nuclear Instruments and Methods in Physics Research A, www.elsevier.com/locate/nima, 0168-9002, doi:10.1016/J.nima.2010.02.066, 2010, Elsevier, Germany.

A.La Rosa, G.Mazza, M.Donetti, F.Marchetto, L.Luetto, A.Attili, F.Bourhaleb, R.Cirio, M.A. Garella, S.Giordanengo, N. Givehchi, S.Iliescu, J.Pardo, A.Pecka, C.Peroni, G.Pitta', Design and test of a 64-channel charge measurement ASIC developed in CMOS 0.35 µm technology, www.sciencedirect.com, Nuclear Instruments and Methods in Physics Research A 583 (2007), pp. 461-468, www.elsevier.com/locate/nima, doi:10.1016/J.nima.2007.09.024, Italy.

H.F.-W.Sadrozinski, M.Baselga, S.Ely, V.Fadeyev, Z.Galloway, J.Ngo, C.Parker, D.Schumacher, A.Seiden, A.Zatserklyaniy, N.Cartiglia, G.Pellegrini, P.Fernandez-Martinez, V.Greco, S. Hildago, D.Quirion, Sensor for ultra-fast silicon detectors, Nuclear Instruments and Methods in Physics Research A, vol. 765 (2014) pp. 7-11, www.elsevier.com/locate/nima, 0168-9002, http://dx.doi.org/10.1016/j.nima.2014.05.006.

* cited by examiner

DEVICES FOR THE SIMULTANEOUS MEASUREMENT IN REAL TIME OF ENERGY AND OF FLUX OF MONO-ENERGETIC BEAMS OF HADRONS OF LOW ENERGY

CROSS-REFERENCE TO RELATED APPLICATIONS

This application is a National Phase Application of PCT International Application No. PCT/IB2015/054383, International Filing Date, Jun. 10, 2015 claiming priority to Italian Patent Application No. TO2014A000464 filed Jun. 10, 2014, each of which is hereby incorporated by reference in its entirety.

FIELD OF THE INVENTION

The present invention generally relates to measurement systems used for determining, in real time and in a non-destructive manner, the characteristics of the radiation field of a beam of particles, in particular in the field of hadron therapy.

BACKGROUND OF THE INVENTION

In this sector, the use is known of systems for monitoring the therapeutic beam, associated with the system for distribution of the dose of the machines for hadron therapy, for the measurement in real time of the flux of particles, of the position and of the profile of the beam in the plane transverse to the direction of propagation of the same beam. For reasons of safety, these monitoring systems are disposed in the immediate vicinity of the patient and make the measurement in a redundant, independent, fashion and lead to a minimum interference on the beam itself. These systems do not however measure the energy of the particles of the beam; they are limited to measuring its position and its profile, in the plane perpendicular to the propagation, whereas the flux is determined indirectly through the measurement of the electric charge produced by ionization in the gas of suitable ionization chambers and via a dosimetric calibration of the said chambers to be periodically carried out through measurements of doses in suitable dummy systems, with certified dosimetries, at the various energies of the beam.

Generally speaking, the energy of the particles of the beam is regulated by fixing the energy of extraction of the beam from the source (particle accelerator) via a suitable configuration of the accelerator, or by controlling appropriate equipment provided along the line of propagation of the beam in order to modulate the energy of the latter. The energy of the particles is thus a pre-defined parameter of the system for production of the beam. The need is however pointed out to integrate into the monitoring system previously described an independent measurement of the energy of the particles of the beam, in order to allow a greater safety in hadron therapy treatments.

This need arises from the new requirements, having come to the fore in the medical field and in the process of being defined in international standards, for guaranteeing to the patient an even higher margin of safety on the exact depth of penetration of the beam into tissues, determined by the energy of the particles, and on the number of particles delivered during the irradiation. For this purpose, the presence is required of at least two independent monitoring systems, each one being capable of measuring the number of particles passing through it and their mean energy, with the capability of interrupting the treatment if these values do not correspond to those required in the planning phase of the treatment.

Specifically, the clinical requirements are to guarantee in real time, during the execution of the treatment and for each beam directed onto the patient, an experimental uncertainty on the depth into the tissue at which the dose is deposited of less than 1 mm (corresponding to the uncertainty in the position of the interface between healthy tissue and tumor-infected tissue to be treated), and an uncertainty on the dose of radiation released equal to or less than 1%.

The need for a new system for monitoring the beams is further reinforced by the observation that the prior art does not allow a simultaneous measurement in real time and in a non-destructive manner of both the energy and of the number of particles delivered by a hadron beam with a precision on the number of particles and on their mean energy so as to guarantee the clinical requirements previously described.

The publication "Design and characterization of the beam monitor detectors of the Italian National Center for Oncological Hadron-therapy (CNAO)" by S. Giordanengo et al. (Nuclear Instruments & Methods in Physics Research. Section A: Accelerators, Spectrometers, Detectors, and Associated Equipment, vol. 698, pages 202-207, XP028958886) describes a system for measuring a mono-energetic hadron beam, comprising a first detection unit which supplies a particle count and a second detection unit which supplies an output signal proportional to the total charge delivered by the beam.

The publication "Diamond detectors for the monitoring of carbon-ion therapy beams" by M. Rebisz-Pomorska et al. (Nuclear Instruments & Methods in Physics Research. Section A: Accelerators, Spectrometers, Detectors, and Associated Equipment, Elsevier BV North-Holland, NL, vol. 620, no. 2-3, pages 534-539, XP027143627) describes a system comprising a single diamond detector designed to measure the number of particles and the energy of the beam in real time.

SUMMARY OF THE INVENTION

In view of the aforementioned requirements, one subject of the invention is a system for the simultaneous measurement of the number of particles transported and the mean energy of a mono-energetic beam of hadrons with characteristics such that there is no significant interference with the beam of particles passing through it and for carrying out the measurement with a precision so as to guarantee an uncertainty on the depth of absorption of the dose into the tissue of less than 1 mm and on the absolute value of the dose absorbed of less than 1%.

Such a measurement instrument includes:
a first detection unit, comprising a planar sensor having a sensing area segmented into a matrix of pixels, each pixel being capable of supplying a signal indicative of the transit of a single particle therethrough, a counting circuit coupled to the sensor for providing an output signal indicative of the number of particles $N_p$ of the beam crossing said sensing area within a given time interval, based on the transit signals provided by the said pixels,
a second detection unit, arranged downstream of the first detection unit, comprising at least one ionization detector capable of supplying an output signal proportional to the total charge $Q_{ion}$ released by the beam in the ionization detector within the same time interval as for the preceding point, and a processing unit designed to receive the output signals from the first and from the second detection units and to determine the mean energy of the beam <E> as a function of the mean ionization energy per particle $S=E_{ion}/N_p$, defined as the ratio between total ionization energy $E_{ion}$ and number of particles $N_p$, the total ionization energy $E_{ion}$ being a function of the total charge $Q_{ion}$ released by the beam in the ionization detector.

Each of the said first and second detection units has a thickness of material $\Delta x_1$, $\Delta x_2$ traversed by the beam, expressed in radiation and interaction length units, of order of magnitude equal to or less than 1/100.

Furthermore, the said first detection unit is capable of obtaining a relative uncertainty $\Delta N_p/N_p$ on the number of detected particles traversing it of order of magnitude equal to or less than 1/1000, and the said second detection unit has a sensitivity $\Delta Q_{ion}$ with which the total charge $Q_{ion}$ is measured of order of magnitude equal to or less than 100 fC. As will be explained in the following, such characteristics of the detection units offer the possibility of controlling the characteristics of the radiation field of the beam of particles in such a manner as to have, in accordance with the recent clinical requirements, an uncertainty on the depth of absorption of the dose of less than 1 mm and on the dose released of less than 1%.

Although the present invention has been designed with particular reference to the monitoring systems for machines for hadron therapy, it may also be applied in other sectors in which the simultaneous measurement is required of energy and flux of a mono-energetic beam of hadrons with an energy below 250-300 MeV.

Another subject of the invention is a method for measuring a mono-energetic beam of hadrons, comprising the following steps:

directing the beam through a first detection unit comprising a planar sensor having a sensing area segmented into a matrix of pixels, each pixel being capable of supplying a signal indicative of the transit of a single particle therethrough, and a counting circuit coupled to the sensor for providing an output signal indicative of the number of particles $N_p$ of the beam crossing said sensing area within a time interval, based on the transit signals provided by said pixels, directing the beam through a second detection unit, arranged downstream of the first detection unit and comprising at least one ionization detector for providing an output signal proportional to total charge $Q_{ion}$ released by the beam in the ionization detector within said time interval, and determining the mean energy of the beam <E> as a function of the mean ionization energy per particle $S=E_{ion}/N_p$, defined as the ratio between the total ionization energy $E_{ion}$ and the number of particles $N_p$, the total ionization energy $E_{ion}$ being a function of the total charge $Q_{ion}$ released by the beam (B) in the ionization detector, wherein each of said first and second detecting units has a material thickness $\Delta x_1$, $\Delta x_2$ crossed by the beam, expressed in radiation and interaction length units, of order of magnitude equal to or less than 1/100.

Further features and advantages of devices, systems and methods according to the invention will become more clearly apparent from the following detailed description of one embodiment of the invention, presented with reference to the attached drawings, provided purely by way of non-limiting examples.

DETAILED DESCRIPTION

Figure 1:
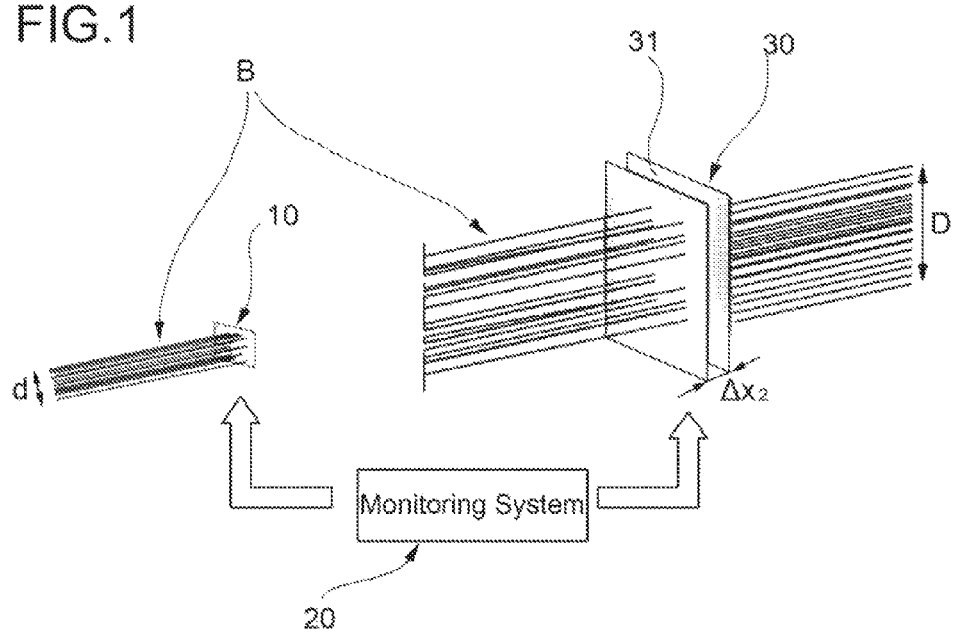
FIG. 1 is a conceptual diagram which shows a system for the measurement of a mono-energetic beam of hadrons.

With reference to FIG. 1, a beam of particles is globally indicated by B. The beam of particles B is a beam of hadrons, in particular of protons, or ions. In the example shown in FIG. 1, along its path, the beam B initially has a certain transverse cross-section d and successively acquires a transverse cross-section D such that D>d. For example, in the case of a beam produced by a machine for hadron therapy, for the beam with initial cross-section d, this could be the beam at the output of the scanning magnets, whereas for the beam with an enlarged cross-section D this could be the beam behind the patient under treatment.

Figure 2:
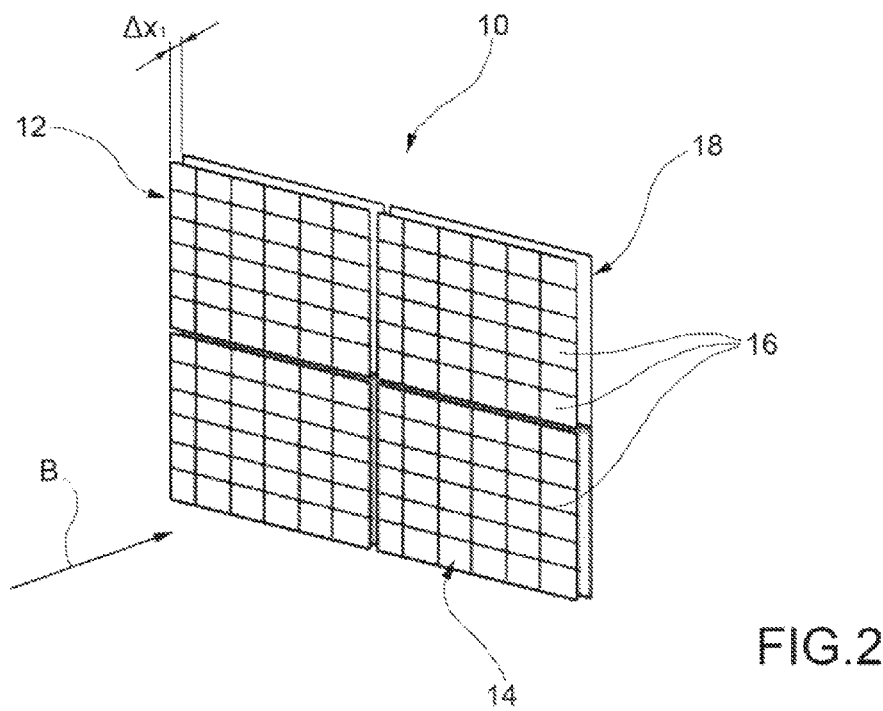
FIG. 2 is a schematic view of a planar detector of the system in FIG. 1.

A system for measuring the beam is associated with the beam B. Such a system comprises a first detection unit 10 (also shown in FIG. 2) arranged in the path of the beam B with a sensing area of large enough dimensions to completely intercept it. The first detection unit 10 comprises a planar sensor 12 having a sensing area 14 segmented into a matrix of pixels 16. Each pixel 16 is capable of supplying a signal indicative of the transit of a single particle of the beam B therethrough. A counting circuit 18 is coupled to the sensor 12 so as to provide an output signal indicative of the number of particles $N_p$ of the beam crossing the sensing area 14 within a time interval, based on the transit signals provided by the pixels 16.

The first detection unit 10 thus constitutes a particle counter. In particular, such a counter must have the following characteristics:

I. The pixels must have small dimensions, in particular between 50 and 500 μm, in order to reduce the probability of two particles impacting the same pixel at the same time. For example, for a beam with a uniform flux rate of $10^{11}$ particles/(cm²*s), and assuming a dead time of the detector of 5 ns, in order to obtain an uncertainty on the number of particles of less than 1/1000, the pixels must have dimensions less than around 100×100 μm².

II. Having a short dead time, in particular of the order of nanoseconds, in order to measure high-intensity beams with a minimal loss of efficiency.

III. Having a fraction of spurious signals and an inefficiency of detection less than a ten thousandth ($10^{-4}$). This value is determined by the requirement to know the number of particles in the beam with a precision of less than one in a thousand.

IV. Being resistant to radiation, namely of complying with requirements 1)-3) for particle fluxes up to $10^{15}$ particles/cm².

A particle counter compatible with the requirements listed above can be implemented using a hybrid technology, with the coupling between a multi-pixel avalanche diode with low internal gain and a read chip using VLSI technology.

The low-gain avalanche diode LGAD [1] can be formed by an ultra-fast silicon detector (UFSD) [2, 3, 4, 5].

These detectors are multi-pixel silicon detectors with a doping layer that generates a multiplication of the signal of around 10 times. These detectors have been developed in order to improve the measurement of the time of passage of a particle, but is provided by the applicant in this application in the innovative function of particle counters. These detectors:

1) are commonly thin (50-100 μm), and thus generate a signal of very short duration, highly suited to measuring high frequencies of passage of particles through the detector without the corresponding signals overlapping;
2) by virtue of the multiplication, in spite of their reduced thickness, they produce a signal of amplitude comparable with the standard multi-pixel detectors, and thus they have an optimum signal-to-noise ratio;
3) they can be used for measuring the time of passage of a particle with a precision of 10-20 ps.

A detector of the UFSD type of 100 μm thickness has a charge signal of around 80 k electrons (assuming a gain ~10), an acquisition time of around 2 ns, and a total time for the signal of around 5 ns [5]. It is thus highly suited to the construction of the counter for the system according to the invention. The invention is not however limited to such a type of device: it is possible to also envisage an analogue sensor based on diamond rather than silicon. Diamond in fact satisfies the I-V points hereinabove, but produces a signal around 3 times lower than a silicon detector of equal thickness. The advantage of diamond is that it is highly resistant to radiation, hence very well adapted to beams of particles with fluxes also 10-100 times higher than those currently in use in hadron therapy.

As far as the counting circuit 18 is concerned, this may be formed by a read chip as mentioned above. Such a read chip may be connected to the sensor by means of the bump-bond technique, creating in this way a hybrid detector, in other words formed by a sensor and a read chip of the same dimensions, superposed and in contact through the bump-bonds. The read chip is thus also traversed by the beam and must accordingly be thin (less than 100 micrometers) so as not to introduce an excessive perturbation of the beam.

The read chip may be formed using a technology of the CMOS type, with a minimum design dimension, for example, of 128 or 65 nanometers.

It goes without saying that the read chip also has to be constructed using a technology that is resistant to radiation.

The read chip is divided into pixels which follow the segmentation of the sensor, in such a manner that each pixel of the sensor is read in an independent manner.

In order to discriminate the passage of a particle, it is preferable for the threshold of the counter to be around 10 times the noise level (or higher), in order to minimize spurious counts. From past experience, it turns out that it is possible to have a noise of around 300 electrons, for which a threshold value of the counter of around 3000 electrons guarantees an ample safety factor against spurious signals. Given that, with the aforementioned characteristics of the sensor, the amplitude of the signal is around 80 k electrons, an efficiency close to 100% is expected.

Taking into account the current tendency of the technology towards the integration between electronics and sensors within the same silicon substrate, an implementation of the particle counter using "monolithic" detectors may also be envisaged, in which the sensor and the read circuit are formed within the same silicon substrate.

From what has been said above, each read channel (in other words each pixel) disposes of its own independent counter, which counts the number of signals arriving between the START and STOP signals.

With the detection unit 10 is accordingly associated a processing and monitoring unit 20 that determines, at the end of a preset time interval, the total number $N_p$ of particles of the beam which have passed through the sensing area, obtained by summing the counts from all the pixels of the sensor. For example, in the case of the application to hadron therapy, the number of counts may be read at regular intervals of time of one microsecond. The processing and monitoring unit 20 may be a device based on FPGA.

Advantageously, the first detection unit 10 is placed wherever the beam B has reduced dimensions; in this way, it is possible to use a very compact device.

The system for measuring the beam B furthermore comprises a second detection unit 30 arranged along the path of the beam B downstream of the first detection unit 10, wherever the beam B may have larger dimensions or else may be deviated into different positions. Also, the second detection unit is arranged so as to intercept the whole beam B. For example, in the case of the application in hadron therapy, the second detection unit will be positioned behind the patient and its sensing area will be greater than the maximum dimensions planned for the area of treatment.

The second detection unit 30 comprises at least one ionization detector 31 capable of supplying an output signal proportional to the total ionizing charge $Q_{ion}$ released by the beam B in an ionizable medium of the ionization detector.

In particular, the ionization detector is an ionization chamber of the parallel plate type, which operates in air or in nitrogen. These chambers, with fluxes of $10^{10}$-$10_{11}$ particles/s, give rise to acquisition efficiencies higher than 99.9% [6].

The read electronics for the charge acquired at the anode of the detector can be based on the current-frequency conversion of a counter which, on the basis of the number of counts recorded within the time interval, supplies the measurement of the charge produced by ionization in the gas from the passage of the particles of the beam[7]. In this case, as will be clearly seen in the following, the charge corresponding to one count should be of the order of 100 fC.

The processing and monitoring unit 20 also receives the signal supplied by the second detection unit 30, indicative of the total ionization charge $Q_{ion}$ released by the particles of the beam B, converts this value into total energy $E_{ion}$ released by the beam in the ionizable medium and calculates the mean ionization energy per particle $S=E_{ion}/N_p$, equal to the ratio between the total ionization energy $E_{ion}$ and the number of particles $N_p$.

Using the curve of energy loss of one particle of the beam B in the ionizable medium of the ionization detector, dE/dx, the processing unit 20 determines from S the mean energy <E> of the particles in the beam B. For this purpose, the beam subjected to measurement must be a beam of low energy, i.e. such that its energy is less than that necessary to be at the minimum for ionization. Under such conditions, there is in fact a strong correlation between the mean loss of energy per ionization S and the energy of the particles <E>. For example, in the case of a beam of protons, the condition indicated hereinabove is verified for an energy of the beam below 250 MeV.

One feature of the subject of the invention is that both the first and the second detection unit have a thickness $\Delta x_1$, $\Delta x_2$ of material traversed by the beam in radiation and interaction length units of the order less than or equal to $1/100$, so as not to alter substantially the dimension, the path and the energy of the beam itself. In particular, each of the thicknesses $\Delta x_1$, $\Delta x_2$ must be less than 5% of the radiation and interaction length of the beam in the materials in question.

From the measurement of the number of particles $N_p$ of the beam which transit within a given time interval through the first detector, and from the total charge $Q_{ion}$ released, within the same interval of time, by the beam in the ionizable medium of the ionization detector, it is possible to get back to the value of the mean energy of the particles of the beam <E>, in the event that the energy of these particles is less than the minimum for ionization. The system according to the invention therefore allows both the flux and the energy of the beam of particles to be measured in real time without significantly altering the characteristics of the beam itself and at the same time guaranteeing an uncertainty on the depth of absorption of the dose of less than 1 mm and on the dose released of less than 1%.

The requirement to have an uncertainty on the depth of absorption of the dose of less than 1 mm and on the dose released of less than 1% is reflected in the characteristics both of the particle counter and of the ionization chamber.

Figure 3:
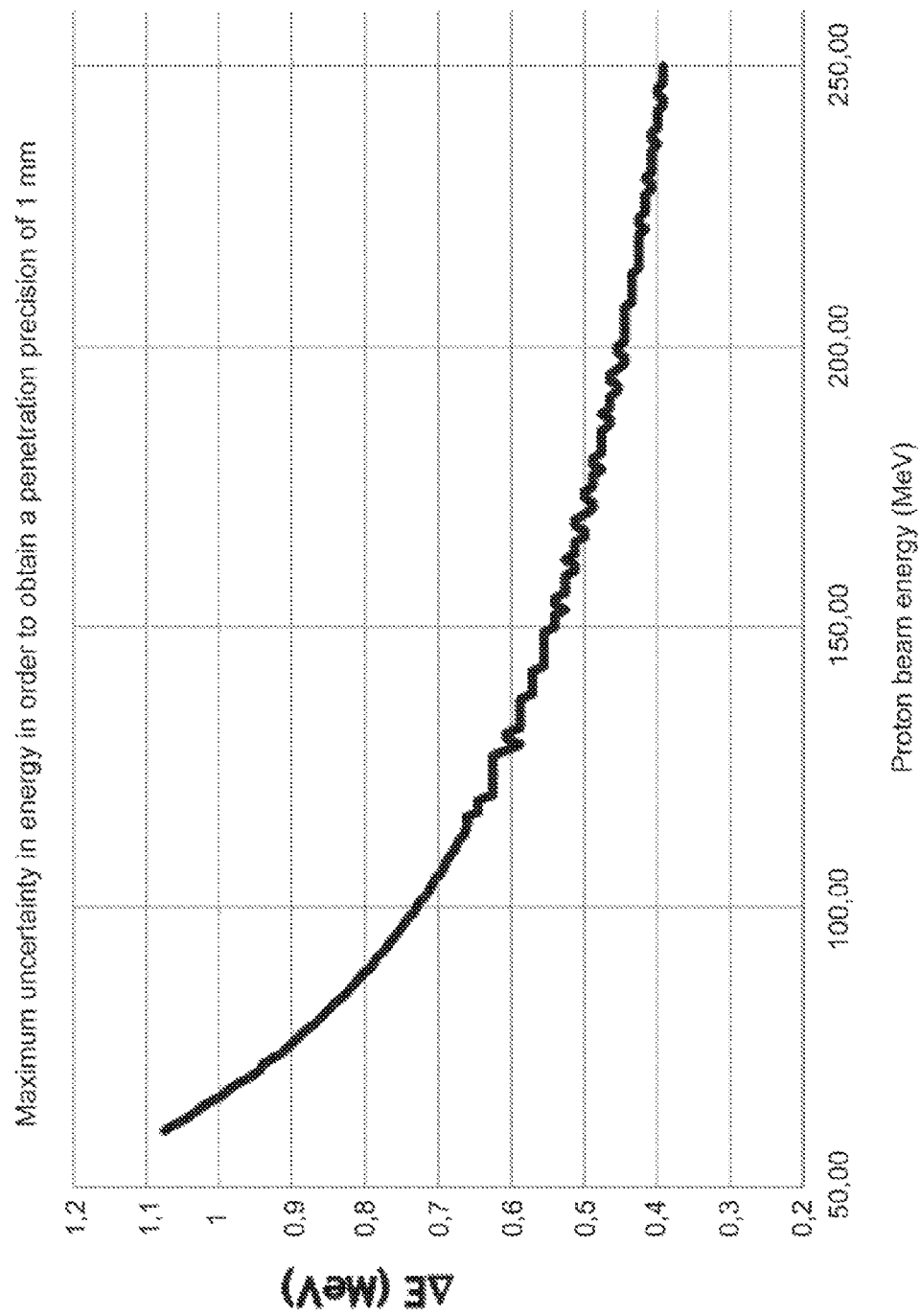
FIG. 3 is a graph showing the maximum allowable uncertainty $\Delta E$ in the measurement of the energy of a beam of protons as a function of the energy of the beam, calculated so as to have a maximum uncertainty of penetration of the particles equal to 1 mm.

The precision needed in the measurement of the mean energy of the particles of the beam, in order to be assured that the depth of penetration is within 1 mm from the desired position, is shown in FIG. 3 as a function of energy. As can be observed, it is the beam with the most energetic particles, 250 MeV, that requires the highest precision, $\Delta E_{min} \sim 400$ keV. Assuming a linear relationship between the mean energy of the particles, <E>, and the mean energy S lost per ionization by a particle in the ionization chamber, it is obtained that the uncertainty on the measurement of the energy lost per ionization must be:

$$\Delta S/S = \Delta E_{min}/<E> < 0.4/250 = 0.16\% \sim 1/1000.$$

$\Delta S$ depends both on the uncertainty $\Delta N_p$ in the number of the particles conveyed by the beam, and on the sensitivity $\Delta Q_{ion}$ with which the total ionizing charge released in the ionizable medium is measured (understood to mean the smallest value of the ionization charge that the detector is capable of detecting):

$$(\Delta S/S)^2 = (\Delta Np/Np)^2 + (\Delta Q_{ion}/Q_{ion})^2$$

for which both ($\Delta Np/Np$) and ($\Delta Q_{ion}/Q_{ion}$) must be of the order of $1/1000$.

Such conditions will be satisfied in the event that the particle counter is capable of providing a relative uncertainty on the number of particles passing through it of less than $1/1000$, assuming a beam flux of $10^{10}$ protons/s and it being desired to perform the measurement within a time of less than 2 ms, the sensitivity $\Delta Q_{ion}$ is 100 fC. More generally, the sensitivity $\Delta Q_{ion}$ should be of the order equal to or less than 100 fC.

Such conditions furthermore guarantee an uncertainty on the dose released well below 1%.

In a typical hadron therapy therapeutic treatment with an active scanning technique, the patient is irradiated with mono-energetic beams, each directed at one slice of the tumour volume localized at a depth corresponding to the depth of penetration of the beam with the energy used. Each slice is irradiated by defining a grid of points and displacing the treatment beam between one point and the next at very short intervals of time, of the order of a millisecond. The system according to the invention can thus be capable of supplying the number of particles and their mean energy at the end of each time interval (and thus for each point of the grid), certifying that the patient has received the dose required by the treatment plan before moving to the next treatment point.

This certification is available, with the present invention, in a time of less than 2 ms for a beam with a flux of $10^{10}$ protons/s.

BIBLIOGRAPHY

[1] G. Pellegrini et al., Technology developments and first measurements of low gain avalanche detectors (LGAD) for high energy physics applications, in Proceedings of HSTD9—International "Hiroshima" Symposium on the Development and Application of Semiconductor Tracking Detectors, Hiroshima Japan, 1-5 Sep. 2013.
[2] H. F.-W. Sadrozinski, N. Cartiglia et al., "Exploring charge multiplication for fast timing with silicon sensors", 20th RD50 Workshop, Bari, Italia, 30 maggio—1° June 2012.
[3] H. F.-W. Sadrozinski, N. Cartiglia et al., "Ultra-Fast Silicon Detectors", Nucl. Instrum. Meth. A 730 (2013), 226-231.
[4] H. F.-W. Sadrozinski, N. Cartiglia et al., "Sensors for Ultra-Fast Silicon Detectors", http://indico.cern.ch/conferenceTimeTable.py?confid=228876#all.
[5] N. Cartiglia et al., "A parameterization of Ultra-Fast Silicon Detector performance", Siena 2013, http://www.bo.infn.it/sminiato/siena.html.
[6] S. Giordanengo et al. "Design and characterization of the beam monitor detectors of the Italian National Center for Oncological Hadron-therapy (CNAO)", Nucl. Instrum. Meth. A 698 (2013), 202-207.
[7] A. The Rosa et al. "Design and test of a 64-channel charge measurement ASIC developed in 0.35 mm CMOS technology", Nucl. Instrum. Meth. A 583 (2007), 461-468.

The invention claimed is:
1. A system for measuring a mono-energetic hadron beam, comprising
a first detection unit which comprises a planar sensor having a sensing area segmented into a matrix of pixels, each pixel being adapted to provide a transit signal indicative of transit of a particle therethrough, and a counting circuit coupled to the sensor for providing an output signal indicative of number of particles $N_p$ of the beam crossing said sensing area in a time interval, based on the transit signals provided by said pixels,
a second detection unit arranged downstream of the first detection unit which comprises at least one ionization detector for providing an output signal proportional to the total charge $Q_{ion}$ released by the beam (B) in the ionization detector in said time interval, and
a processing unit designed to receive the output signals from the first and from the second detection unit,
wherein each of said first and second detection units has a material thickness $\Delta x1$, $\Delta x2$ crossed by the beam, expressed in radiation and interaction length units, of order of magnitude equal to or less than $1/100$,
and wherein said processing unit is designed to determine mean beam energy <E> as a function of mean ionization energy per particle $S = E_{ion}/N_p$, defined as the ratio of total ionization energy $E_{ion}$ to number of particles $N_p$, the total ionization energy $E_{ion}$ being function of the total charge $Q_{ion}$ released by the beam (B) in the ionization detector.

2. The system of claim 1, wherein said planar sensor comprises a multi-pixel, low gain avalanche diode.

3. The system of claim 1, wherein said ionization detector comprises an ionization chamber.

4. The system of claim 1, wherein said processing unit is adapted to determine the mean beam energy <E> as a function of the mean ionization energy per particle $S=E_{ion}/N_p$, from energy loss function of a particle of the beam (B) in a ionizable medium of the ionization detector.

5. A method for measuring a mono-energetic hadron beam, comprising:
 conveying the beam through a first detection unit which comprises a planar sensor having a sensing area segmented into a matrix of pixels, each pixel being adapted to provide a transit signal indicative of transit of a particle therethrough, and a counting circuit coupled to the sensor for providing an output signal indicative of number of particles $N_p$ of the beam crossing said sensing area in a time interval, based on the transit signals provided by said pixels, and
 conveying the beam (B) through a second detection unit arranged downstream of the first detection unit which comprises at least one ionization detector for providing an output signal proportional to total charge $Q_{ion}$ released by the beam (B) in the ionization detector in said time interval,
 wherein each of said first and second detection units has a material thickness $\Delta x_1$, $\Delta x_2$ crossed by the beam, expressed in radiation and interaction length units, of order of magnitude equal to or less than $1/100$,
 and further comprising
 determining mean beam energy <E> as a function of mean ionization energy per particle $S=E_{ion}/N_p$, defined as the ratio of total ionization energy $E_{ion}$ to number of particles $N_p$, the total ionization energy $E_{ion}$ being function of the total charge $Q_{ion}$ released by the beam (B) in the ionization detector.

6. The method of claim 5, wherein the mean beam energy <E> is determined from energy loss function of a particle of the beam (B) in the ionizable medium of the ionization detector.

7. The method of claim 5, wherein said planar sensor comprises a multi-pixel, low gain avalanche diode.

8. The method of claim 5, wherein said ionization detector comprises an ionization chamber.

* * * * *